(12) United States Patent
Shanklin et al.

(10) Patent No.: US 6,686,186 B2
(45) Date of Patent: Feb. 3, 2004

(54) MUTANT FATTY ACID DESATURASE

(75) Inventors: John Shanklin, Shoreham, NY (US); Edgar B. Cahoon, Wilmington, DE (US)

(73) Assignee: Brookhaven Science Associates LLC, Upton, NY (US)

( * ) Notice: Subject to any disclaimer, the term of this patent is extended or adjusted under 35 U.S.C. 154(b) by 16 days.

(21) Appl. No.: 09/988,929

(22) Filed: Dec. 3, 2001

(65) Prior Publication Data

US 2002/0150982 A1 Oct. 17, 2002

Related U.S. Application Data

(63) Continuation-in-part of application No. 09/233,856, filed on Jan. 19, 1999, now abandoned.

(51) Int. Cl.$^7$ .......................... C12N 9/02; C12N 15/29; C12N 5/14; C07H 21/04
(52) U.S. Cl. ............... 435/189; 435/252.3; 435/254.11; 435/320.1; 435/325; 435/410; 536/23.2
(58) Field of Search .............................. 435/189, 252.3, 435/254.11, 320.1, 325, 410; 536/23.2

(56) References Cited

U.S. PATENT DOCUMENTS

| | | | | |
|---|---|---|---|---|
| 5,614,400 A | | 3/1997 | Cahoon et al. | 435/172.3 |
| 5,705,391 A | * | 1/1998 | Cahoon et al. | 435/419 |
| 5,856,157 A | | 1/1999 | Craig et al. | 435/189 |
| 5,888,790 A | * | 3/1999 | Cahoon et al. | 435/172.3 |
| 6,100,091 A | | 8/2000 | Cahoon et al. | 435/189 |

OTHER PUBLICATIONS

Shanklin and Cahoon, *Annu. Rev. Plant Physiol. Plant Mol. Biol.* 49: 611–641 (1998).
Thompson et al., *Proc. Natl. Acad. Sci. USA* 88: 2578–2582 (1991).
Clark et al., *Biochemistry* 22: 5897–5902 (1983).
Cahoon et al., *Proc. Natl. Acad. Sci. USA* 94: 4872–4877 (1997).
Whittle et al., *J. Biol. Chem.* 276:21500–21505 (2001).
Zhao, H. and Arnold, F. H. (1997) Current Opinion in Structural Biology 7:210–241: Combinatorial protein design: strategies for screening protein libraries.
Oliphant, A. R. and Struhl, K. (1989) Proc. Natl. Acad. Sci. USA 86:9094–9098: An efficient method for generating proteins with altered enzymatic properties: Application to β–lactamase.
Giver, L., Gershenson, A., Freskgard, P–O., and Arnold, F. H. (1998) Proc. Natl. Acad. Sci. USA 95:12809–12813: Directed evolution of a thermostable esterase.
Cahoon, E. B., Mills, L. A., and Shanklin, J. (1996) J. Bacteriology 178:936–939: Modification of the Fatty Acid Composition of *Escherichia coli* by Coexpression of a Plant Acyl–Acyl Carrier Protein Desaturase and Ferredoxin.

* cited by examiner

*Primary Examiner*—Tekchand Saidha
(74) *Attorney, Agent, or Firm*—Margaret C. Bogosian

(57) ABSTRACT

The present invention relates to a method for producing mutants of a fatty acid desaturase having a substantially increased activity towards fatty acid substrates with chains containing fewer than 18 carbons relative to an unmutagenized precursor desaturase having an 18 carbon atom chain length substrate specificity. The method involves inducing one or more mutations in the nucleic acid sequence encoding the precursor desaturase, transforming the mutated sequence into an unsaturated fatty acid auxotroph cell such as MH13 *E. coli*, culturing the cells in the absence of supplemental unsaturated fatty acids, thereby selecting for recipient cells which have received and which express a mutant fatty acid desaturase with an elevated specificity for fatty acid substrates having chain lengths of less than 18 carbon atoms. A variety of mutants having 16 or fewer carbon atom chain length substrate specificities are produced by this method. Mutant desaturases produced by this method can be introduced via expression vectors into prokaryotic and eukaryotic cells and can also be used in the production of transgenic plants which may be used to produce specific fatty acid products.

31 Claims, 1 Drawing Sheet

FIGURE 1

```
  1   ASTLKSGSKE  VENLKKPFMP  PREVHVQVTH  SMPPQKIEIF   40
 41   KSLDNWAEEN  ILVHLKPVEK  CWQPQDFLPD  PASDGFDEQV   80
 81   RELRERAKEI  PDDYFVVLVG  DMITEEALPT  YQTMLNTLDG  120
121   VRDETGASPT  SWAIWTRAWT  AEENRHGDLL  NKYLYLSGRV  160
161   DMRQIEKTIQ  YLIGSGMDPR  TENSPYLGFI  YTSFQERATF  200
201   ISHGNTARQA  KEHGDIKLAQ  ICGTIAADEK  RHETAYTKIV  240
241   EKLFEIDPDG  TVLAFADMMR  KKISMPAHLM  YDGRDDNLFD  280
281   HFSAVAQRLG  VYTAKDYADI  LEFLVGRWKV  DKLTGLSAEG  320
321   QKAQDYVCRL  PPRIRRLEER  AQGRAKEAPT  MPFSWIFDRQ  360
361   VKL                                             363
```

SEQ ID NO: 1

MUTANT FATTY ACID DESATURASE

The present application is a continuation-in-part of U.S. patent application Ser. No. 09/233,856 filed on Jan. 19, 1999 now abandoned.

This invention was made with Government support under contract number DE-AC02-98CH10886, awarded by the U.S. Department of Energy. The Government has certain rights in the invention.

BACKGROUND OF THE INVENTION

Fatty acid biosynthesis in higher plants has recently attracted increased interest because of the possible use of plant oils as renewable sources for reduced carbon. The diversity of fatty acid forms in wild plants is vast compared to that of crop plants. This diversity is reflected in the variations in chain length, the number and position of double bonds, and the position and occurrence of a variety of other functional groups in the fatty acids of wild plants.

In plants, fatty acid biosynthesis occurs in the chloroplasts of green tissue or in the plastids of non-photosynthetic tissues. The primary products in most plants are acyl carrier protein (ACP) esters of the saturated palmitic (palmitoyl-ACP) and/or stearic (stearoyl-ACP) acids, palmitic acid having a 16 carbon atom chain length and stearic acid having an 18 carbon atom chain length. Two types of desaturase molecules are involved in the production of monounsaturated fatty acids (monoenes), soluble, and integral membrane proteins. Desaturases are specific for a particular substrate carbon atom chain length (chain length specificity) and introduce the double bond between specific carbon atoms in the chain (double bond positional specificity) by counting from the carboxyl end of the fatty acid. For instance, the castor $\Delta^9$-18:0 desaturase is specific for stearoyl-ACP, and introduces a double bond between carbon atoms 9 and 10.

The introduction of non-native desaturase isoforms having unique characteristic chain length and double bond positional specificities into agricultural crops offers a way to manipulate the content, physical properties and commercial uses of plant-produced oils. Unfortunately, the introduction of non-native acyl-ACP desaturase isoforms into agricultural crop plants has yet to lead to the efficient production of unusual monoenes by agricultural crop plants. An alternative way in which to accomplish the manipulation of the content, physical properties and commercial uses of oilseed crops would be through the introduction of a native desaturase which had been manipulated in such a way as to alter its chain length and/or double bond positional specificities.

As the genes encoding more desaturase enzymes are identified it is becoming apparent that many of the different activities are derived from relatively few common archetypes encoding the soluble and membrane classes of desaturases. Molecular modeling and X-ray crystallographic studies of soluble acyl-ACP desaturases have identified amino acid residues within the substrate binding channel which are in very close proximity to the fatty acid substrate. Such residues are referred to as "contact residues". That earlier research demonstrated that certain modifications of one or more contact residues and modification of some non-contact residues can alter the chain-length and double bond positional specificities of acyl-ACP desaturases in vitro (Cahoon, et al. Proc. Natl. Acad. Sci. USA (1997) 94:4872–4877 and Cahoon, et al. U.S. Pat. Nos. 5,705,391, 5,888,790 and 6,100,091). Those studies were carried out using predictions formulated from the three dimensional structure of the castor $\Delta^9$-18:0 acyl-ACP desaturase in combination with alignment of its sequence with that of a $\Delta^6$-16:0 acyl-ACP desaturase as well as with the sequences of other 18:0 desaturases. The studies examined the effects of replacing specific contact and non-contact amino acid residues of one enzyme with the amino acid in the cognate position of the other enzyme on the in vitro substrate chain length and double bond positional specificities of several desaturase enzymes. The studies demonstrated that substituting a major portion of the substrate binding channel of a $\Delta^9$-18:0 desaturase into the homologous position of a $\Delta^6$-16:0 desaturase converted its in vitro specificity to that of a $\Delta^9$-18:0 desaturase. This could also be accomplished by replacing five specific amino acids of the $\Delta^6$-16:0 desaturase with five amino acids of the $\Delta^9$-18:0 desaturase which occupy homologous positions. It was also shown that substituting bulky amino acids (isoleucine for proline at position 179 and phenylalanine for leucine at position 118) into the substrate binding channel of the $\Delta^9$-18:0 desaturase increased its preference for the 16:0-ACP substrate such that the in vitro 16:0-ACP activity became slightly more than two-fold greater than its remaining 18:0-ACP activity.

The ability to manipulate the chain length and double bond position specificities of desaturases has great potential with regard to generation and use of mutated native desaturases in the production of commercially useful products, such as vegetable oils rich in monounsaturated fatty acids. Such vegetable oils are important in human nutrition. In addition, because a double bond in an otherwise saturated carbon chain is readily susceptible to chemical modification, fatty acid chains having double bonds in unique positions produced by crop plants can be useful raw materials for industrial processes.

The earlier studies making use of molecular modeling and crystallographic data, while successful, were extremely time consuming and the in vitro activity of the altered enzymes was not directly correlated to the in vivo specificities of the altered enzymes. Those studies pointed out a need for a simplified and general method for readily producing mutants of desaturases which have altered and desirable chain length and double bond positional specificities.

SUMMARY OF THE INVENTION

The present invention relates to a simple and general method for producing a mutant of a fatty acid desaturase, the original desaturase having an 18 carbon atom chain length substrate specificity, the mutant produced having substantially increased activity relative to the original desaturase towards fatty acid substrates with chains containing fewer than 18 carbons. The method involves inducing one or more mutations in the nucleic acid sequence encoding the original desaturase, transforming the mutated nucleic acid sequence under conditions for expression into a cell which normally requires a growth medium that is supplemented with unsaturated fatty acids in order to proliferate (i.e., an unsaturated fatty acid auxotroph cell), and then selecting for recipient cells which have received a mutant fatty acid desaturase with a specificity for shorter carbon atom chain length substrates. In a preferred embodiment, the mutated nucleic acid sequences are transformed into an E. coli unsaturated fatty acid auxotroph designated MH13. The cells are then grown in the absence of added unsaturated fatty acids to select for recipient MH13 cells which express mutated enzymes which are capable of producing sufficient unsaturated fatty acids in the cell to support growth, thereby overcoming the auxotrophy. Other aspects of the present invention include the mutants which are produced. Mutants of castor Δ⁹-18:0-ACP desaturase produced by the method arise from amino acid substitutions at specific residues. These mutants each have altered substrate chain length specificity, of 16- or fewer carbon atoms. Other embodiments of the present invention encompass the expression of the mutant desaturase molecules in individual cells and also in transgenic plants, for the production of specific fatty acid products.

BRIEF DESCRIPTION OF THE DRAWINGS

FIG. 1 lists the amino acid sequence (SEQ ID NO: 1) of mature Δ⁹-18:0-ACP castor desaturase enzyme.

DETAILED DESCRIPTION OF THE INVENTION

The present invention is based on the use of a bacterial selection system for the selection of mutant desaturase molecules which have 18-carbon atom chain length substrate specificities prior to the introduction of the mutation and which have a 16 or fewer carbon atom chain length substrate specificity of as a result of the mutation. A preferred bacterial strain used in the selection system, *E. coli* MH13, is an unsaturated fatty acid auxotroph. MH13 normally requires a growth medium that is supplemented with unsaturated fatty acids in order to proliferate. Previous research (Cahoon, et al., (1996) J. Bacteriology 178:936–939 and Thompson, et al. (1991) Proc. Natl. Acad. Sci. USA 88:2578–2582) demonstrated that although 14:0 and 16:0 acyl-ACP desaturases were able to use in vivo pools of acyl-ACPs in *E. coli* to produce monounsaturated fatty acids, Δ⁹-18:0 acyl-ACP desaturases do not generate detectable amounts of monounsaturated fatty acids when expressed in *E. coli*. Thus, due to the substrate pools of saturated fatty acid substrates in *E. coli*, the Δ⁹-18:0 desaturase enzymes are not sufficiently active in the *E. coli* host cell and are thus not able to complement the deficiency in unsaturated fatty acid auxotrophs such as *E. coli* MH13. Desaturase enzymes which specifically utilize 18-carbon chain length substrates cannot complement the auxotrophy due to the low levels of such 18-carbon chain length substrates in the bacterial cell. However, introduction of a functional desaturase enzyme which has substantial activity towards fatty acid substrates with chains containing 16 or fewer carbons will complement this auxotrophy, allowing for the growth and proliferation of the bacteria in the absence of supplemental unsaturated fatty acids. These observations have been exploited as a selection system for identifying mutants of an 18-carbon specific fatty acid desaturase which have a substantially increased activity towards fatty acid substrates with chains containing 16 carbons or 14 carbons. While *E. coli* MH13 is a preferred host cell, one of skill in the art will recognize that other host cell types may be employed.

The present invention provides for a method of producing a mutant of a fatty acid desaturase, the mutant being characterized as having a specificity for shorter chain length fatty acid substrates compared to the original fatty acid desaturase. The method requires nucleic acid sequences encoding a fatty acid desaturase with 18 carbon atom chain length substrate specificity. To produce the mutant, mutations are induced in the nucleic acid sequence encoding the fatty acid desaturase. The mutated nucleic acid sequence is then transformed into the MH13 *E. coli* cells under conditions appropriate for expression of the mutated sequence. The transformed MH13 *E. coli* cells are then selected for the ability to grow in the absence of supplemental unsaturated fatty acids. Survival of a transformed MH13 *E. coli* indicates the acquisition of a mutant fatty acid desaturase which complements the fatty acid auxotrophy of MH13 because of its altered chain length specificity. A mutant fatty acid desaturase identified by the above selection assay has a substantial increase in the activity towards fatty acid substrates with chains containing fewer than 18 carbons, relative to the original desaturase. A substantial increase in substrate specificity with respect to the original desaturase is one that produces sufficient accumulation of unsaturated fatty acids, which results from desaturation by the mutant desaturase, within an unsaturated fatty acid auxotroph host organism so as to support growth and proliferation of the host organism. Substantial increase in activity sufficient to support growth of the auxotroph host is at least three-fold higher than that of the non-mutagenized precursor desaturase. In a preferred embodiment, the increase in activity of the mutant desaturase is at least ten-fold higher than the non-mutagenized precursor desaturase.

The Exemplification section below details experiments where the method was used to identify mutants of castor A9-18:0-ACP desaturase with modified substrate specificities. One of skill in the art will recognize that the method is suitable for producing mutants of any fatty acid desaturase which has an 18 carbon atom chain length substrate specificity prior to mutagenesis. To do so requires only a nucleic acid sequence for the desaturase. Expression of the nucleic acid sequence results in the production of a mature fatty acid desaturase, and following mutagenesis of the nucleic acid sequence, those sequences which are mutated to cause the alteration in the chain length specificity of enzyme will be expressed and identified through the selection procedure.

The nucleic acid sequences having silent mutations which do not affect the amino acid sequence of the translated product would not be identified in the selection procedure. Nucleic acid sequences encoding a functional fatty acid desaturase, whose amino acid sequence varies from wild type, for example with conservative amino acid substitutions that do not affect function in regard to carbon chain length substrate specificity would also not be identified in the selection procedure. However, such mutated desaturases may be desirable when incorporating several different functional mutations into one mutant.

In preferred embodiments, the fatty acid desaturase is a plant fatty acid desaturase. There are two types of plant fatty acid desaturases, soluble (acyl-ACP desaturases), and integral membrane (acyl lipid desaturases), both of which are suitable for use in the present invention.

In one embodiment, the MH13 *E. coli* also express an exogenous plant ferredoxin. This can be accomplished by introduction of an expression vector containing sequences which encode plant ferredoxin (e.g. Arabaena vegetative ferredoxin), and the application of selective pressure to the resulting bacteria. The presence of plant ferredoxin, the redox partner of the plant desaturases, facilitates the function of the plant desaturase in *E. coli*. The presence of plant ferredoxin in the selection system allows for the selection of mutants with low specific activities towards fatty acids with 16 or fewer carbon atoms. Mutants which complement MH13 in the absence of plant ferredoxin are expected to have comparatively higher specific activities toward the shorter fatty acid substrates (Cahoon, et al. (1996)).

The selection system described above is most appropriate for use in selecting mutants with the desired substrate specificity from a heterogeneous population of mutant fatty acid desaturase molecules. By transforming a population of mutated nucleic acid sequences into the auxotroph host cells, entire libraries of mutants can be screened for the ability to complement the MH13 auxotrophy.

Any type of mutation which has the potential to result in a modified fatty acid desaturase protein product can be induced in the nucleic acid sequences. Logic based approaches of introducing amino acid substitutions into residues which interact with substrate are sound but can be very labor intensive and are mainly suited to cases in which structural information is available. Such methods have been successfully employed for modifying the chain length specificity of soluble desaturases, and for the introduction of double-bond versus hydroxyl group for the membrane class of enzymes (Cahoon et al., (1997); Shanklin, et al. (1998) Annu. Rev. Plant Physiol. Plant Mol Biol. 49:611–641). Experiments described in the Exemplification section which follows demonstrate a form of site directed mutagenesis which specifically targets a particular codon, or codons, to produce amino acid randomization at specific position(s) within the protein product. These experiments also describe utilization of random mutagenesis, which has the potential to identify additional amino acids involved in substrate specificity. The use of random mutagenesis is perhaps the most powerful method because it does not rely on assumptions about which residues are important, assumptions which are based on structural information. The present method has the ability to identify substitution mutations at positions which are amino acid contact residues (positions which are located nearest the substrate within the binding channel) and also positions which affect the substrate specificity without directly contacting the substrate (Cahoon et al., (1997)).

Once mutated, the nucleic acid sequences are transformed into the MH13 cells. Transformation is preferably accomplished by electroporation, but alternative methods known to one of skill in the art can also be used.

Following transformation, the cells are selected for the presence of the mutant fatty acid desaturase. This is accomplished by growth on selective media (e.g. media which is not supplemented with unsaturated fatty acids). The media can be either solid or liquid. Using several rounds of selection, and/or varying or augmenting the selective pressures involved is also useful in increasing the number of mutants identified by the method.

The present invention is useful in the engineering of desaturase proteins with characteristic substrate chain length preferences. Such isoforms, when introduced into cells or organisms, (e.g. agricultural crops) can be used to manipulate the physical properties and commercial uses of conventional plant oils. Cells and organisms which express these engineered desaturases are useful in the production of commercially useful products, such as vegetable oils rich in monounsaturated fatty acids, which have many potential uses, for example in human nutrition or as industrial chemicals.

The Exemplification section below details experiments where the above described method was used to identify mutants of castor $\Delta^9$-18:0-ACP desaturase with modified substrate specificities. Mutations which result in amino acid substitutions at position 114, 117, 118, 179, 181, or 188, and combined substitutions at positions 114 and 188 are described, along with the resulting change in specificity of these mutant proteins compared to wild type. The listed amino acid substitutions made at the analogous positions in other ACP-desaturases, especially in 18:0-ACP desaturases, and preferably in $\Delta^9$-18:0-ACP desaturases, are predicted to have the analogous effects on substrate specificity.

The mutants produced can be inserted into a DNA expression vector, which can be used to express the mutants in cells. Expression vectors which function in either and/or both prokaryotic and eukaryotic cells exist and are known to those of skill in the art. The appropriate expression vectors are introduced into either prokaryotic cells (e.g. bacteria) and also eukaryotic cells (e.g. animal cells or plant cells) to promote expression of the mutant proteins. Plant cells which express the mutant proteins can be used to produce transgenic plants which express the mutant proteins, and which produce the corresponding fatty acid products of the desaturases.

Exemplification

A mutagenesis and selection approach was employed to identify amino acid substitution mutations in fatty acid desaturases which modify substrate specificity. Acyl-ACP desaturases are functionally active when expressed in *E. coli*. $\Delta^9$-18:0-ACP desaturases are unable to alter the fatty acid profile of *E. coli* due to a lack of appropriate substrate (Thompson et al., (1991)). However, desaturases with 16:0 or 14:0 specificity were shown to alter the fatty acid profile of *E. coli* (Cahoon, et al. (1996)). Thus, 18:0 desaturases cannot complement the *E. coli* mutant MH13, an unsaturated fatty acid auxotroph, but desaturases with specificities for fatty acids with 16 or fewer carbons are able to complement this auxotrophy. Thus, the MH13 *E. coli* strain was used to select for mutants of an 18-carbon atom-specific desaturase which can utilize 16- or 14-carbon atom substrates in a complementation assay.

To facilitate the function of a plant acyl-ACP desaturase in *E. coli*, an expression vector containing the gene for plant ferredoxin, the redox partner of the plant desaturase, was transformed into the MH13 *E. coli* and maintained under selective pressure. These cells, MH13(pACYC/LacAnFd), were used in the following experiments.

The nucleic acid sequence for castor $\Delta^9$-18:0-ACP desaturase was subjected to one of two types of mutagenesis, site directed or random mutagenesis, prior to introduction into the MH13 cells. PCR was used in site directed mutagenesis to randomize a targeted codon corresponding to a specified residue in the amino acid sequence of the castor-$\Delta^9$-18:0-ACP desaturase. Target codons corresponding to Met 114, Leu 118, Pro 179, and Gly 188 were each subjected to independent randomization. Previous studies (Cahoon, et al. (1997)) had indicated that these residues are located adjacent to the substrate binding cavity and that replacing some of those amino acids in the T. alata $\Delta^6$-16:0 desaturase or in the castor $\Delta^9$-18:0 desaturase with bulkier or less bulky amino acids could affect substrate specificity in vitro. The methods of the present invention allowed for an unbiased substitution of all 20 amino acids into these positions but required that the mutation affect the in vivo substrate specificity of the desaturase. The mutagenesis reactions yielded four populations, each one comprising a library of coding sequences with substitution mutations consisting of all 20 potential amino acids at the designated mutation site.

To examine whether mutations in additional contact and or non-contact amino acid residues could alter the in vivo substrate specificity of the castor $\Delta^9$-18:0 desaturase, a totally unbiased approach using random mutagenesis was performed on sequences encoding castor $\Delta^9$-18:0-ACP desaturase by single gene DNA shuffling.

MH13 (pACYC/LacAnFd) were transformed with the resulting libraries of mutated 18:0-ACP desaturase nucleic acid sequences, under conditions appropriate for expression, and then selected for expression of a mutant with the ability to complement the unsaturated fatty acid auxotrophy, by growth in the absence of supplemental unsaturated fatty acid. To confer survival under the selective conditions, a mutant desaturase would necessarily have an altered substrate chain length specificity of 16, 14 or fewer carbons. The selection for site directed mutants was performed in either liquid media or on agar plates. The selection for randomly generated mutants was performed on agar plates. Growth in liquid media involved several rounds of dilution and re-growth to enrich for mutations that resulted in the best complementation.

In a variation on the site directed mutagenesis, mutants were selected from a library encoding all 400 possible combinations of amino acids at position 188 and 114, two adjacent contact residues within the substrate binding channel. This was achieved by excising a restriction fragment from the open reading frame of the library encoding all possible amino acids at position 188 and inserting this fragment into the equivalent plasmid population randomized for position 114. Using this method, mutant M114I-G188L was identified in the selection procedure. The coding sequences of the selected desaturases were sequenced to identify the specific mutations which conferred complementation to the fatty acid auxotrophy. The substrate specificities of the identified mutants were determined by in vitro enzyme assays (Cahoon et al., (1997)). Table 1 lists the identified mutations and the altered chain length substrate specificity conferred.

TABLE 1

| | Mutagenesis method | | Fold change in specificity with respect to wt | |
|---|---|---|---|---|
| Position | Directed | Random | 16:18 | 14:18 |
| Met 114 | Ile (16) | Ile (16) | 6 | |
| Met 114 | Phe (14)/ Tyr (14) | | Phe 7 | 490 |
| Thr 117 | | Ile (16) | not determined | |
| Leu 118 | Phe (16)/ Tyr (16) | Phe (16)/ Met (16) | Tyr 130 | |
| Pro 179 | Ile (16) | Leu (14) | 20 | |
| Thr 181 | | Ile (16) | not determined | |
| Gly 188 | Leu (16) | | 740 | |
| Met 114—Gly188:M114I—G188L (16) | | | 1410 | |

Mutations obtained hy mutagenesis/selection numbers in parentheses represent the chain length specificity that is most enhanced with respect to the wt castor $\Delta^9$-18:0 desaturase activity. Shown are also the fold change in specificity ratios where known. For instance, if the activity with respect to 16 carbon was increased by 10-fold, and the activity with respect to 18:0 was decreased by 5-fold, the "Fold change in specificity with respect to wt" for 16:18 would be 50.

The designated amino acid positions above correspond to the mature castor enzyme as defined in Lindqvist et al., EMBO J 15:4081–4092 (1996), the sequence (SEQ ID NO: 1) of which is listed in FIG. 1.

While the use of structure-guided (i.e., directed) mutagenesis of residues M114, L118, P170 and G188 was effective for the identification of seven mutants with anticipated the levels of desired fatty acids will increase in the homozygous T2 plants. These results suggest that mutants derived from castor $\Delta^9$-18:0-ACP desaturase may be useful for future metabolic engineering of oil crops.

Methods of the Invention

Cell lines. The *E. coli* unsaturated fatty acid auxotroph MH13 mutant of *E. coli* K12 (Henry, M. F., Ph.D. Thesis (1992) University of Illinois, Urbana-Champaign) is a fadR:Tn5 mutant of cell line DC308 (Clark et al. (1983) Biochemistry 22:5897–5902) which was constructed by phage P1 transduction from strain RS3069 (Simons et al. (1980) J. Bacteriol. 142:621–632). MH13 requires a medium supplemented with unsaturated fatty acids at all growth temperatures due to a temperature-sensitive lesion in fabA and transposon disruption of fadR. An XbaI/EcoRI fragment from a pET9d expression plasmid containing the coding sequence of Anabaena vegetative ferredoxin (Fd) (Cheng et al. (1995) Arch. Biochem. Biophys. 316:619–634) was inserted into the corresponding sites of pLac3d to generate the plasmid pLacAnFd. pLac3d is analogous to pET3d except that the T7 RNA polymerase promoter has been replaced with the lacUV5 promoter of *E. coli* RNA polymerase as described previously (Cahoon et al. (1996)). A BglII/HindIII fragment from pLacAnFd was then inserted into the BamHI/HindIII sites of substrate specificities of 16 or fewer carbons, the method relied on the appropriate choice of target residues for mutagenesis. It is well documented that residues that affect substrate specificity fall into two broad classes, direct and indirect. Thus, random mutagenesis selection provides a bias-free method for the identification of changes that result in increased specificity for shorter acyl chains. Through random mutagenesis and selection, five amino acid positions were identified, three at sites that were also targets for the structure-guided mutagenesis, and two new sites, T117 and T181, were identified.

Naturally occurring 16:0-ACP desaturases from Milkweed and Doxantha have very poor activities when assayed in vitro (31 and 3 nM/min/mg, respectively). By comparison, the selected mutant G188L has an activity of (175 nM/min/mg), much closer to that of the parental wild type castor $\Delta$9-18:0-ACP desaturase for its 18:0-ACP substrate.

To test whether the altered enzymes identified in the selection assay would result in the accumulation of unusual fatty acids when expressed in plants, the G188L mutant was introduced into *Arabidopsis thaliana* (fab1 background) using a napin promoter to drive expression. The first generation of G188L transgenics (T1) produced seeds which contained approximately 10% of fatty acids modified by the introduced desaturase. Because T1 seeds are heterozygous it is pACYC184. This construct (pACYC/LacAnFd) was then introduced into MH13 cells by electroporation. Complementation Analysis/Selection. The *E. coli* MH13 strain harboring pACYC/LacAnFd was used as a host for expression of acyl-ACP desaturases. For these studies, the coding sequence of wild type and mutant mature acyl-ACP desaturases were inserted into pLac3d. Cells were transformed with the resulting plasmid constructs and were then grown on plates or in liquid broth containing Luria-Bertani (LB) media with ampicillin (100 μg/ml), chloramphenicol (35 μg/ml), and kanamycin (40 μg/ml) selection. For non-selective growth, plates were supplemented with the fatty acid oleic acid solubilized in Tergitol NP-40 (Sigma) with final concentrations of 250 μg/ml oleic acid and 2% (v/v) Tergitol. Liquid broth was supplemented with oleic acid (solubilized in Tergitol NP-40) at a final concentration of 100 μg/ml. Oleic acid was initially prepared as 1000× stock solution in ethanol and solubilized in melted Tergitol, prior to addition to the media. Media used to test for complementation of the auxotrophy did not contain added oleic acid, and IPTG was added at a concentration of 0.4 mM to induce expression of acyl-ACP desaturase from the expression vector.

Transformation. Transformation was conducted by electroporation using a 50 μl aliquot of competent MH13 cells harboring pACYC/LacAnFd and 0.1 to 0.5 μg of expression plasmid for a given acyl-ACP desaturase. Following electroporation, cells were resuspended in 500 μl of LB media and shaken (250 rpm) at 37° C. for 45 min to 1 h. Cells were then plated on media as described above. Alternatively, a 75 μl aliquot of the transformed cells was added to 25 ml of LB media containing IPTG and antibiotics at concentrations described above. These cells were then maintained with shaking at 30° or 37° C.

Electrocompetent MH13 (pACYC/LacAnFd) were prepared by growing a culture from a single colony in low-salt LB media (10 mg/ml Bacto tryptone, 5 mg/ml yeast extract, and 5 mg/ml sodium chloride) containing kanamycin (40 μg/ml) and chloramphenicol (35 μg/ml) and supplemented with oleic acid (100 μg/ml) and 2% Tergitol (v/v). Cells were prepared for transformation and electroporated as described in the BioRad protocol for high efficiency electro-transformation of *E. coli*.

Mutagenesis. Two methods were used for mutagenesis. The first, site directed mutagenesis, randomized a target residue at a specific location in the amino acid sequence of the castor $\Delta^9$-18:0-ACP desaturase. Four target residues were chosen: Met 114, Leu 118, Pro 179, and Gly 188. PCR was used to generate four populations of DNA. Each population consisted of sequences encoding castor $\Delta^9$-18:0-ACP desaturase with a randomized codon for residue 114, 118, 179, or 188. Each of the four populations was generated using PCR site directed mutagenesis to produce DNA products having equimolar proportions of each of the four nucleotides at each position of the target codon. For each of the four randomized products, an oligonucleotide primer was synthesized which hybridized to sequences adjacent to the target codon, and contained a randomized codon in place of the target codon sequences, the primer population containing equimolar proportions of each of the four nucleotides G, A, T, and C at the three positions within the replacement codon. This primer was used in conjunction with a primer homologous to the 5' terminus of the gene to amplify the gene segment between the two primer binding sites. A second overlapping fragment was then synthesized using PCR to amplify the remainder of the respective coding sequences of the four PCR reaction products. The fragments were then incorporated into larger gene fragments using overlap extension polymerase chain reaction (Ho, et al. (1989) Gene 77: 51–59). The gene fragments containing the randomized target codons were inserted into pLac3.

The second mutagenesis method introduced random mutations into the coding region sequence by digesting the castor $\Delta^9$-18:0-ACP desaturase coding region with DNase, and reassembling using PCR (W. P. Stemmer (1994) Proc Natl Acad Sci USA 91:10747–10751). The entire coding region was reinserted into pLac3 to make a library of pLac3-castor-$\Delta^9$-18:0-ACP desaturase genes with random mutations throughout the coding region.

What is claimed is:

1. A method for producing a collection of individual mutant 18 carbon atom-specific fatty acid desaturase enzymes, each having a substantial increase in activity towards fatty acid substrates with chains containing fewer than 18 carbon atoms, comprising:
   a) providing a nucleic acid sequence encoding a fatty acid desaturase having an 18 carbon atom chain length specificity;
   b) inducing mutations in the nucleic acid sequence of step a);
   c) transforming the mutated nucleic acid sequence of step b) into appropriate unsaturated fatty acid auxotroph host cells;
   d) culturing the transformed cells of step c) under selective conditions which conditions are also appropriate for expression of said mutated nucleic acid sequence;
   e) separating and culturing individual isolates of the transformed cells that grow under the selective conditions of step d); and
   f) separately purifying the mutant desaturases from the isolates of step e), said mutant fatty acid desaturases each having a substantial increase in activity towards fatty acid substrates with chains containing fewer than 18 carbon atoms, relative to the fatty acid desaturase encoded by the nucleic acid sequence of step a).

2. The method of claim 1 wherein the fatty acid auxotroph host cell is MH13 *E. coli*.

3. The method of claim 2 wherein the mutant fatty acid desaturase is characterized by the ability to complement the fatty acid auxotrophy of the MH13 *E. coli*.

4. The method of claim 2 wherein the MH13 *E. coli* fatty acid auxotroph expresses exogenous ferredoxin.

5. The method of claim 4 wherein the exogenous ferredoxin is Arabaena vegetative ferredoxin.

6. The method of claim 5 wherein the MH13 *E. coli* expressing Arabaena vegetative ferredoxin is MH13 (pACYC/LacAnFd).

7. The method of claim 1 wherein the fatty acid desaturase is a plant fatty acid desaturase.

8. The method of claim 7 wherein the plant fatty acid desaturase is an integral membrane protein.

9. The method of claim 8 wherein the integral membrane protein fatty acid desaturase is an acyl lipid desaturase.

10. The method of claim 7 wherein the plant fatty acid desaturase is a soluble protein.

11. The method of claim 10 wherein the soluble plant fatty acid desaturase is an acyl-ACP desaturase.

12. The method of claim 11 wherein the acyl-ACP desaturase is castor $\Delta^9$-18:0-ACP desaturase.

13. The method of claim 1 wherein the mutant fatty acid desaturase catalyzes desaturation of 16-carbon atom fatty acids.

14. The method of claim 1 wherein the mutant fatty acid desaturase catalyzes desaturation of 14-carbon atom fatty acids.

15. The method of claim 1 wherein the mutant fatty acid desaturase catalyzes desaturation of 12-carbon atom fatty acids.

16. The method of claim 1 wherein the mutant fatty acid desaturase catalyzes desaturation of 10-carbon atom fatty acids.

17. The method of claim 1 wherein the mutations of step b) are induced by random mutagenesis.

18. The method of claim 17 wherein the random mutations are induced in an acyl-ACP desaturase nucleic acid sequence.

19. The method of claim 1 wherein the mutations of step b) are induced by site directed mutagenesis at one or more codons.

20. The method of claim 19 wherein the site specific mutations are induced in an acyl-ACP desaturase nucleic acid sequence at one or more codons.

21. The method of claim 20 wherein one or more codons specific for amino acid contact residues are mutated.

22. The method of claim 20 wherein one or more codons specific for amino acids which are not contact residues are mutated.

23. The method of claim 1 wherein transformation of the host cell is by electroporation.

24. The method of claim 1 wherein the selection of step d) is performed in liquid media.

25. The method of claim 1 wherein the selection of step d) is performed on solid media.

26. The method of claim 2 wherein the mutated nucleic acid sequence is inserted into the expression vector pLac3 prior to transformation into the MH13 *E. coli*.

27. The method of claim 1 wherein the fatty acid auxotroph host cell is characterized as having an unaltered fatty acid profile following introduction of an 18 carbon atom-specific desaturase into the cell and having an altered fatty acid profile following introduction of a 16:0 desaturase, a 14:0 desaturase, a 12:0 desaturase or a 10:0 desaturase into the cell.

28. The method of claim 1 wherein said nucleic acid sequence of step a) is an 18:0 desaturase sequence obtained from the group consisting of castor, brassica, sunflower, yellow lupine, cotton, coriander, maize, sesame, rice, flax, safflower, avocado and cucumber.

29. The method of claim 7 wherein the plant is selected from the group consisting of castor, brassica, sunflower, yellow lupine, cotton, coriander, maize, sesame, rice, flax, safflower, avocado and cucumber.

30. The method of claim 24 wherein the liquid media lacks added unsaturated fatty acids.

31. The method of claim 25 wherein the solid media lacks added unsaturated fatty acids.

* * * * *

SEQUENCE LISTING

<160> NUMBER OF SEQ ID NOS: 1

<210> SEQ ID NO 1
<211> LENGTH: 363
<212> TYPE: PRT
<213> ORGANISM: Ricinus communis

<400> SEQUENCE: 1

```
Ala Ser Thr Leu Lys Ser Gly Ser Lys Glu Val Glu Asn Leu Lys Lys
1               5                   10                  15

Pro Phe Met Pro Pro Arg Glu Val His Val Gln Val Thr His Ser Met
            20                  25                  30

Pro Pro Gln Lys Ile Glu Ile Phe Lys Ser Leu Asp Asn Trp Ala Glu
        35                  40                  45

Glu Asn Ile Leu Val His Leu Lys Pro Val Glu Lys Cys Trp Gln Pro
    50                  55                  60

Gln Asp Phe Leu Pro Asp Pro Ala Ser Asp Gly Phe Asp Glu Gln Val
65                  70                  75                  80

Arg Glu Leu Arg Glu Arg Ala Lys Glu Ile Pro Asp Asp Tyr Phe Val
                85                  90                  95

Val Leu Val Gly Asp Met Ile Thr Glu Glu Ala Leu Pro Thr Tyr Gln
            100                 105                 110

Thr Met Leu Asn Thr Leu Asp Gly Val Arg Asp Glu Thr Gly Ala Ser
            115                 120                 125

Pro Thr Ser Trp Ala Ile Trp Thr Arg Ala Trp Thr Ala Glu Glu Asn
            130                 135                 140

Arg His Gly Asp Leu Leu Asn Lys Tyr Leu Tyr Leu Ser Gly Arg Val
145                 150                 155                 160
```

-continued

```
Asp Met Arg Gln Ile Glu Lys Thr Ile Gln Tyr Leu Ile Gly Ser Gly
            165                 170                 175

Met Asp Pro Arg Thr Glu Asn Ser Pro Tyr Leu Gly Phe Ile Tyr Thr
            180                 185                 190

Ser Phe Gln Glu Arg Ala Thr Phe Ile Ser His Gly Asn Thr Ala Arg
            195                 200                 205

Gln Ala Lys Glu His Gly Asp Ile Lys Leu Ala Gln Ile Cys Gly Thr
        210                 215                 220

Ile Ala Ala Asp Glu Lys Arg His Glu Thr Ala Tyr Thr Lys Ile Val
225                 230                 235                 240

Glu Lys Leu Phe Glu Ile Asp Pro Asp Gly Thr Val Leu Ala Phe Ala
            245                 250                 255

Asp Met Met Arg Lys Lys Ile Ser Met Pro Ala His Leu Met Tyr Asp
            260                 265                 270

Gly Arg Asp Asp Asn Leu Phe Asp His Phe Ser Ala Val Ala Gln Arg
            275                 280                 285

Leu Gly Val Tyr Thr Ala Lys Asp Tyr Ala Asp Ile Leu Glu Phe Leu
            290                 295                 300

Val Gly Arg Trp Lys Val Asp Lys Leu Thr Gly Leu Ser Ala Glu Gly
305                 310                 315                 320

Gln Lys Ala Gln Asp Tyr Val Cys Arg Leu Pro Pro Arg Ile Arg Arg
            325                 330                 335

Leu Glu Glu Arg Ala Gln Gly Arg Ala Lys Glu Ala Pro Thr Met Pro
            340                 345                 350

Phe Ser Trp Ile Phe Asp Arg Gln Val Lys Leu
            355                 360
```